(12) United States Patent
Xie et al.

(10) Patent No.: US 11,578,027 B2
(45) Date of Patent: Feb. 14, 2023

(54) METHOD FOR PRODUCING A POLYURETHANE POLYMER

(71) Applicant: Milliken & Company, Spartanburg, SC (US)

(72) Inventors: Chunping Xie, Shanghai (CN); Zhaolin Zhou, Singapore (SG); Xiaodong Zhao, Shanghai (CN); Hong Chen, Shanghai (CN)

(73) Assignee: Milliken & Company, Spartanburg, SC (US)

( * ) Notice: Subject to any disclaimer, the term of this patent is extended or adjusted under 35 U.S.C. 154(b) by 22 days.

(21) Appl. No.: 17/028,216

(22) Filed: Sep. 22, 2020

(65) Prior Publication Data

US 2021/0002198 A1 Jan. 7, 2021

Related U.S. Application Data

(63) Continuation of application No. 15/277,649, filed on Sep. 27, 2016, now Pat. No. 10,800,723.

(60) Provisional application No. 62/379,944, filed on Aug. 26, 2016, provisional application No. 62/233,713, filed on Sep. 28, 2015.

(51) Int. Cl.
| | |
|---|---|
| *C07C 41/46* | (2006.01) |
| *C08G 18/76* | (2006.01) |
| *C08G 18/66* | (2006.01) |
| *C08L 71/02* | (2006.01) |
| *C08G 18/63* | (2006.01) |
| *C08G 18/64* | (2006.01) |
| *C08G 18/32* | (2006.01) |
| *C07C 43/13* | (2006.01) |
| *C08G 73/02* | (2006.01) |

(52) U.S. Cl.
CPC .............. *C07C 41/46* (2013.01); *C07C 43/13* (2013.01); *C08G 18/3275* (2013.01); *C08G 18/632* (2013.01); *C08G 18/6423* (2013.01); *C08G 18/6688* (2013.01); *C08G 18/7621* (2013.01); *C08G 18/7664* (2013.01); *C08L 71/02* (2013.01); *C08G 73/0206* (2013.01)

(58) Field of Classification Search
CPC ..... C07C 41/46; C07C 43/13; C08G 18/3275; C08G 18/632; C08G 18/6423; C08G 18/6688; C08G 18/7621; C08G 18/7664; C08G 73/0206; C08L 71/02

See application file for complete search history.

(56) References Cited

U.S. PATENT DOCUMENTS

| | | | |
|---|---|---|---|
| 4,082,884 A | 4/1978 | De Long | |
| 4,892,719 A | 1/1990 | Gesser | |
| 5,284,892 A | 2/1994 | Brodie, III | |
| 5,350,788 A | 9/1994 | Visioli | |
| 6,723,836 B1 | 4/2004 | Araki | |
| 2008/0281013 A1 | 11/2008 | Nakamura | |
| 2013/0052113 A1 | 2/2013 | Molins | |
| 2013/0330532 A1* | 12/2013 | Dierschke | C08K 3/26 521/181 |
| 2014/0227544 A1 | 8/2014 | Inoue | |

FOREIGN PATENT DOCUMENTS

| | | |
|---|---|---|
| CN | 1244207 | 2/2000 |
| CN | 101007259 | 8/2007 |
| CN | 101235107 | 8/2008 |
| CN | 101370626 | 2/2009 |
| CN | 101495577 | 7/2009 |
| CN | 102380351 | 3/2012 |
| CN | 103173170 | 6/2013 |
| CN | 104437422 | 3/2015 |
| CN | 104797617 | 7/2015 |
| DE | 69517128 | 1/2001 |
| DE | 10003157 | 8/2001 |
| FR | 2726567 | 5/1996 |
| WO | 2011084463 | 7/2011 |
| WO | 2016022876 | 2/2016 |

OTHER PUBLICATIONS

English Translation of FR-2726567-A1, 21 pages, (Year: 1996).
PCT/US2016/053971 International Search Report, filed Sep. 27, 2016, 4 pages.
PCT/US2016/053971 Written Opinion of the International Searching Authority, filed Sep. 27, 2016, 4 pages.

* cited by examiner

*Primary Examiner* — Andrew J. Oyer
(74) *Attorney, Agent, or Firm* — Robert M. Lanning

(57) ABSTRACT

A method for producing a polyurethane polymer comprises the steps of: (a) providing a polyol composition, the polyol composition comprising (i) a polyol, (ii) a polyethylenimine compound; and (iii) a bisulfite compound, (b) providing an isocyanate compound; (c) providing a catalyst; (d) combining and reacting the polyol composition, the isocyanate compound, and the catalyst to produce a polyurethane polymer.

9 Claims, No Drawings

METHOD FOR PRODUCING A POLYURETHANE POLYMER

CROSS-REFERENCE TO RELATED PATENT APPLICATIONS

This application claims, pursuant to 35 U.S.C. § 120, priority to and the benefit of the filing date of U.S. patent application Ser. No. 15/277,649 filed on Sep. 27, 2016, which application claims, pursuant to 35 U.S.C. § 119(e)(1), priority to and the benefit of the filing date of U.S. Patent Application No. 62/233,713 filed on Sep. 28, 2015 and U.S. Patent Application No. 62/379,944 filed on Aug. 26, 2016, all of which applications are herein incorporated by reference.

TECHNICAL FIELD OF THE INVENTION

This application is directed to compositions and methods for reducing the residual aldehyde content of and foul odors that can be emitted by some polyols. The application also discusses the use of such polyols in the production of polyurethane polymers, such as polyurethane foams.

BACKGROUND

Polyols are used in a variety of industrial processes. For example, polyols are a key raw material in the production of polyurethane polymers. Polyurethane polymers produced from polyols are used in a wide variety of applications, such as the production of polyurethane foams. These polyurethane foams are, in turn, put to many different end uses. For example, polyurethane foams are frequently used as cushioning and padding in, for example, transportation seating (e.g., automobile seating) and furniture, such as mattresses and other cushioned furniture. When these polyurethane foams are used in enclosed environments, such as the interior of an automobile or other vehicle, the foam typically must pass tests that limit the amount of volatile organic compounds that can be released by the foam. The volatile organic compounds emitted by the polyurethane foam during testing can be produced as a by-product of the reaction that produces the polyurethane polymer. The volatile organic compounds (e.g., aldehydes such as formaldehyde, acetaldehyde, and propionaldehyde) can also be present in the raw materials used to make the foam (e.g., the polyol). These volatile organic compounds can also impart undesirable, foul odors to the raw materials. For example, some commercially available polyols suffer from relatively high residual aldehyde content and have a foul odor, both of which make such polyols less desirable to polyurethane producers. Therefore, it would be desirable to find a composition or method that reduces the detectable levels of volatile organic compounds present in these raw materials, such as the polyol. This application seeks to provide such a composition and method.

BRIEF SUMMARY OF THE INVENTION

In a first embodiment, the invention provides a composition comprising:
(a) a polyol; and
(b) a polyethylenimine compound.

In a second embodiment, the invention provides a method for reducing the volatile aldehyde compound content of a polyol, the method comprising the steps of:

(a) providing a polyol, the polyol containing a first amount of volatile aldehyde compounds;
(b) providing a polyethylenimine compound;
(c) adding the polyethylenimine compound to the polyol to produce a composition, wherein the composition contains a second amount of volatile aldehyde compounds, and the second amount of volatile aldehyde compounds is less than the first amount of volatile aldehyde compounds.

DETAILED DESCRIPTION OF THE INVENTION

In a first embodiment, the invention provides a composition comprising a polyol and a polyethylenimine compound.

The composition can comprise any suitable polyol. Suitable polyols include polyether polyols and polyester polyols. Preferably, the polyol is a polyether polyol. Suitable polyether polyols include those made by reacting epoxides, such as ethylene oxide, propylene oxide, butylene oxide, and glycidol, with a multifunctional initiator compound, such as a multifunctional alcohol or amine. Examples of suitable multifunctional initiator compounds include, but are not limited to, water, glycerin, pentaerythritol, ethylene glycol, propylene glycol (e.g., 1,2-propylene glycol), trimethylolpropane, and ethylene diamine.

The polyol can have any suitable molar mass. In a preferred embodiment, the polyol has a molar mass of about 400 g/mol or more. More preferably, the polyol has a molar mass of about 500 g/mol or more, about 750 g/mol or more, or about 1,000 g/mol or more.

The polyol used in making the composition can contain volatile aldehyde compounds, such as formaldehyde, acetaldehyde, and propionaldehyde. While not wishing to be bound to any particular theory, it is believed that these volatile aldehyde compounds can be produced during the production of the polyol itself or by the oxidative degradation of the polyol during storage. Prior to incorporation of the polyethylenimine compound, the untreated polyol can contain as much as 3 ppm or more of volatile aldehyde compounds (e.g., formaldehyde, acetaldehyde, and/or propionaldehyde) based on the weight of the polyol.

The composition can comprise any suitable polyethylenimine compound. The polyethylenimine compound can be a linear polyethylenimine or a branched polyethylenimine. Preferably, the polyethylenimine compound is a branched polyethylenimine. The polyethylenimine can have any suitable degree of polymerization or molar mass. Preferably, the polyethylenimine compound has a molar mass of about 500 g/mol or more. The polyethylenimine compound more preferably has a molar mass about 600 g/mol or more, about 700 g/mol or more, about 800 g/mol or more, about 900 g/mol or more, or about 1,000 g/mol or more.

The polyethylenimine compound can be present in the composition in any suitable amount. The polyethylenimine compound preferably is present in the composition in an amount of about 50 ppm or more, based on the weight of the polyol present in the composition. More preferably, the polyethylenimine compound is present in the composition in an amount of about 75 ppm or more, about 100 ppm or more, about 125 ppm or more, about 150 ppm or more, about 175 ppm or more, about 200 ppm or more, about 300 ppm or more, about 400 ppm or more, or about 500 ppm or more, based on the weight of the polyol present in the composition. The polyethylenimine compound preferably is present in the composition in an amount of about 20,000 ppm or less, about 15,000 ppm or less, about 10,000 ppm or less, about 5,000 ppm or less, about 4,000 ppm or less, or about 3,000 ppm or less, based on the weight of the polyol present in the composition. Thus, in a series of preferred embodiments, the polyethylenimine compound is present in the composition in an amount of about 50 ppm to about 20,000 ppm (e.g., about 100 ppm to about 20,000 ppm, about 150 ppm to about 20,000 ppm, about 200 ppm to about 20,000 ppm, about 300 ppm to about 20,000 ppm, about 400 ppm to about 20,000 ppm, or about 500 ppm to about 20,000 ppm), about 50 ppm to about 15,000 ppm (e.g., about 100 ppm to about 15,000 ppm, about 150 ppm to about 15,000 ppm, about 200 ppm to about 15,000 ppm, about 300 ppm to about 15,000 ppm, about 400 ppm to about 15,000 ppm, or about 500 ppm to about 15,000 ppm), about 50 ppm to about 10,000 ppm (e.g., e.g., about 100 ppm to about 10,000 ppm, about 150 ppm to about 10,000 ppm, about 200 ppm to about 10,000 ppm, about 300 ppm to about 10,000 ppm, about 400 ppm to about 10,000 ppm, or about 500 ppm to about 10,000 ppm), about 50 ppm to about 5,000 ppm, (e.g., about 100 ppm to about 5,000 ppm, about 150 ppm to about 5,000 ppm, about 200 ppm to about 5,000 ppm, about 300 ppm to about 5,000 ppm, about 400 ppm to about 5,000 ppm, or about 500 ppm to about 5,000 ppm), about 50 ppm to about 4,000 ppm, (e.g., about 100 ppm to about 4,000 ppm, about 150 ppm to about 4,000 ppm, about 200 ppm to about 4,000 ppm, about 300 ppm to about 4,000 ppm, about 400 ppm to about 4,000 ppm, or about 500 ppm to about 4,000 ppm), about 50 ppm to about 3,000 ppm, (e.g., about 100 ppm to about 3,000 ppm, about 150 ppm to about 3,000 ppm, about 200 ppm to about 3,000 ppm, about 300 ppm to about 3,000 ppm, about 400 ppm to about 3,000 ppm, or about 500 ppm to about 3,000 ppm), based on the weight of the polyol present in the composition.

As is noted above, the polyethylenimine compound is added to the polyol in order to reduce the volatile aldehyde compounds present in the polyol. For example, it has been observed that addition of a polyethylenimine compound in the amounts described above can reduce the volatile aldehyde compounds present in an untreated polyol by as much as 30% or even more. Thus, in one preferred embodiment, the composition (i.e., the combination comprising the polyol and the polyethylenimine compound) contains about 2 ppm or less of volatile aldehyde compounds, based on the weight of the polyol. In addition to reducing the amount of volatile aldehyde compounds in the polyol, the addition of the polyethylenimine compound has also been observed to reduce foul odors emitted by the polyol. The ability of the polyethylenimine compound to reduce both the measured quantity of volatile aldehyde compounds and the foul odor of the polyol is surprising and unexpected.

The composition can comprise other components in addition to the polyol and the polyethylenimine compound. For example, the composition can comprise a second amine compound. In a preferred embodiment, the composition further comprises tert-butylamine (i.e., 2-methylpropan-2-amine) as the second amine compound. When present in the composition, the second amine compound can be present in any suitable amount. If the second amine compound is present in the composition, the second amine compound preferably is present in the composition in an amount of about 5 ppm or more, based on the weight of the polyol present in the composition. More preferably, the second amine compound preferably is present in the composition in an amount of about 10 ppm or more, about 15 ppm or more, about 20 ppm or more, or about 25 ppm or more, based on the weight of the polyol in the composition.

In certain possibly preferred embodiments, the composition comprises a bisulfite compound in addition to the polyol and the polyethylenimine compound. In a preferred embodiment, the composition further comprises sodium bisulfite. When present in the composition, the bisulfite compound can be present in any suitable amount. The bisulfite compound preferably is present in the composition in an amount of about 50 ppm or more, based on the weight of the polyol present in the composition. More preferably, the bisulfite compound is present in the composition in an amount of about 75 ppm or more, about 100 ppm or more, about 125 ppm or more, about 150 ppm or more, about 175 ppm or more, about 200 ppm or more, about 300 ppm or more, about 400 ppm or more, or about 500 ppm or more, based on the weight of the polyol present in the composition. The bisulfite compound preferably is present in the composition in an amount of about 20,000 ppm or less, about 15,000 ppm or less, about 10,000 ppm or less, about 5,000 ppm or less, about 4,000 ppm or less, or about 3,000 ppm or less, based on the weight of the polyol present in the composition. Thus, in a series of preferred embodiments, the bisulfite compound is present in the composition in an amount of about 50 ppm to about 20,000 ppm (e.g., about 100 ppm to about 20,000 ppm, about 150 ppm to about 20,000 ppm, about 200 ppm to about 20,000 ppm, about 300 ppm to about 20,000 ppm, about 400 ppm to about 20,000 ppm, or about 500 ppm to about 20,000 ppm), about 50 ppm to about 15,000 ppm (e.g., about 100 ppm to about 15,000 ppm, about 150 ppm to about 15,000 ppm, about 200 ppm to about 15,000 ppm, about 300 ppm to about 15,000 ppm, about 400 ppm to about 15,000 ppm, or about 500 ppm to about 15,000 ppm), about 50 ppm to about 10,000 ppm (e.g., e.g., about 100 ppm to about 10,000 ppm, about 150 ppm to about 10,000 ppm, about 200 ppm to about 10,000 ppm, about 300 ppm to about 10,000 ppm, about 400 ppm to about 10,000 ppm, or about 500 ppm to about 10,000 ppm), about 50 ppm to about 5,000 ppm, (e.g., about 100 ppm to about 5,000 ppm, about 150 ppm to about 5,000 ppm, about 200 ppm to about 5,000 ppm, about 300 ppm to about 5,000 ppm, about 400 ppm to about 5,000 ppm, or about 500 ppm to about 5,000 ppm), about 50 ppm to about 4,000 ppm, (e.g., about 100 ppm to about 4,000 ppm, about 150 ppm to about 4,000 ppm, about 200 ppm to about 4,000 ppm, about 300 ppm to about 4,000 ppm, about 400 ppm to about 4,000 ppm, or about 500 ppm to about 4,000 ppm), about 50 ppm to about 3,000 ppm, (e.g., about 100 ppm to about 3,000 ppm, about 150 ppm to about 3,000 ppm, about 200 ppm to about 3,000 ppm, about 300 ppm to about 3,000 ppm, about 400 ppm to about 3,000 ppm, or about 500 ppm to about 3,000 ppm), based on the weight of the polyol present in the composition.

When present in the composition, the amount of bisulfite compound present in the composition can also be expressed relative to the amount of polyethylenimine compound present in the composition. Preferably, the bisulfite compound is present in the composition in an amount of about 0.5 parts by weight or more per 1 part of polyethylenimine compound. The bisulfite compound preferably is present in the composition in an amount of about 2 parts by weight or less per 1 part of polyethylenimine compound. Thus, in a more specific preferred embodiment, the bisulfite compound is present in the composition in an amount of about 0.5 to about 2 parts by weight per 1 part of polyethylenimine compound. In a particularly preferred embodiment, the bisulfite compound is present in the composition in an amount of about 2 parts by weight per 1 part polyethylenimine compound.

As noted above, the invention also provides a method for reducing the amount of volatile aldehyde compounds present in a polyol. In one embodiment, the method comprises the steps of: (a) providing a polyol, (b) providing a polyethylenimine compound; and (c) adding the polyethylenimine compound to the polyol to produce a composition. The polyol contains a first amount of volatile aldehyde compounds, and the composition contains a second amount of volatile aldehyde compounds. The second amount of volatile aldehyde compounds is less than the first amount of volatile aldehyde compounds. In other words, the volatile aldehyde compound content of the polyol has been reduced by the addition of the polyethylenimine compound. The polyol, polyethylenimine compound, and other additional components used in the method can be any of the materials described above in connection with the first embodiment of the invention.

As noted above, the composition of the invention can be used in the production of polyurethane polymers. The composition can be used alone as the sole source of polyol, or the composition can be used in conjunction with one or more other polyols. The polyol or mixture of polyols used in the production of the polyurethane polymer will depend, at least in part, on the desired properties of the polymer. In producing the polyurethane polymer, the composition can be used in combination with any suitable isocyanate compound or combination of isocyanate compounds. Suitable isocyanate compounds include, but are not limited to, toluene diisocyanate and diphenylmethane diisocyanate. Typically, the polyol(s) and the isocyanate compound are reacted in the presence of a catalyst, such as an amine catalyst, an organometallic catalyst (e.g., organotin compounds), or a mixture of the two. Amine catalysts, which are typically tertiary amine compounds, are the most commonly used catalysts in the production of flexible polyurethane foams, such as those used in seating and other cushioning applications. Unfortunately, the use of an amine catalyst can impart an unpleasant or foul odor to the polyurethane polymer. Surprisingly, it has been observed that the polyethylenimine compound contained in the composition of the invention can also reduce the unpleasant odor imparted to the polymer by the use of an amine catalyst.

The following examples further illustrate the subject matter described above but, of course, should not be construed as in any way limiting the scope thereof.

Example 1

This example demonstrates the production of a composition according to the invention.

A commercially available polyol (Sample 1A) was tested to quantify the initial acetaldehyde content. The odor of the polyol was also qualitatively measured by smelling a quantity of the polyol in a container. The initial measurements for both were recorded for later comparison and are set forth in Table 1 below.

Varying amounts of a polyethylenimine compound (having a molar mass of about 2,500 g/mol) were added to the polyol and stirred at room temperature (approximately 22° C.) for approximately one hour. Sample 1J was heated to a temperature of approximately 100° C. and stirred for approximately one hour. A blend of antioxidants (containing a lactone-based antioxidant, a phosphite-based antioxidant, and a hindered phenol antioxidant) was also added to Samples 1C-1J. Tert-butylamine was also added to Samples 1 D-1 G, and a single drop of water was added to Sample 1G. The acetaldehyde content and odor of the resulting compositions was then measured and recorded for comparison to the untreated polyol. These measurements are set forth in Table 1 below.

TABLE 1

Polyethylenimine compound concentration (PEI), antioxidant concentration (AOX), tert-butylamine concentration (TBA), acetaldehyde content (CHO), and odor measurements for Samples 1A-1J.

| Sample | PEI (ppm) | AOX (ppm) | TBA (ppm) | CHO (ppm) | Odor |
|---|---|---|---|---|---|
| 1A | — | — | — | 3.05 | Very pronounced |
| 1B | 520 | — | — | 2.16 | Less pronounced |
| 1C | 10,000 | 2,000 | — | 1.62 | Slightly noticeable |
| 1D | 10,000 | 2,000 | 30 | 1.18 | Slightly noticeable |
| 1E | 500 | 2,000 | 30 | 1.74 | Less pronounced |
| 1F | 200 | 2,000 | 30 | 1.68 | Less pronounced |
| 1G | 200 | 2,000 | 30 | 1.63 | Less pronounced |
| 1H | 200 | 2,000 | — | 1.95 | Less pronounced |
| 1I | 500 | 2,000 | — | 2.01 | Less pronounced |
| 1J | 100 | 2,000 | — | 3.0 | Slightly less pronounced |

As can be seen from the data set forth in Table 1, each of the compositions containing a polyethylenimine compound (Samples 1B-1J) showed lower acetaldehyde concentrations than the virgin, untreated polyol (Sample 1A). These compositions also showed perceptible improvements in odor as compared to the virgin, untreated polyol. The degree of the decrease in acetaldehyde content and odor generally increased with increasing concentrations of the polyethylenimine compound. The addition of tert-butylamine decreased the measured acetaldehyde content of the polyol but did not have a perceptible impact on the odor of the polyol.

Example 2

This example demonstrates the production of a composition according to the invention.

The odor of a commercially available polyol (Sample 2A) was qualitatively measured by smelling a quantity of the polyol in a container. The initial measurement was recorded for later comparison and is set forth in Table 2 below.

Varying amounts of a polyethylenimine compound (having a molar mass of about 2,500 g/mol) were added to the polyol and stirred at room temperature (approximately 22° C.) for approximately one hour. The odor of the resulting compositions was then measured and recorded for comparison to the untreated polyol. These measurements are set forth in Table 2 below.

TABLE 2

Polyethylenimine compound concentration (PEI) and odor measurements for Samples 2A-2C.

| Sample | PEI (ppm) | Odor |
|---|---|---|
| 2A | — | Very pronounced |
| 2B | 10,000 | Slightly noticeable |
| 2C | 1,000 | Less pronounced |

As can be seen from the data set forth in Table 2, each of the compositions containing a polyethylenimine compound (Samples 2B and 2C) showed perceptible improvements in odor as compared to the virgin, untreated polyol (Sample 2A). The degree of the decrease in smell generally increased with increasing concentrations of the polyethylenimine compound.

Example 3

This example demonstrates the production of a composition according to the invention.

A commercially available polyol (Sample 3A) was tested to quantify the initial acetaldehyde content. The initial measurement was recorded for later comparison and is set forth in Table 3 below.

A polyethylenimine compound (having a molar mass of about 2,500 g/mol) was added to the polyol and stirred at room temperature (approximately 22° C.) for approximately one hour. The acetaldehyde content of the resulting composition (Sample 3B) was then measured and recorded for comparison to the untreated polyol. This measurement is set forth in Table 3 below.

TABLE 3

Polyethylenimine compound concentration (PEI) and acetaldehyde content (CHO) for Samples 3A and 3B.

| Sample | PEI (ppm) | CHO (ppm) |
|---|---|---|
| 3A | — | 6.02 |
| 3B | 452 | 2.91 |

As can be seen from the data set forth in Table 3, the composition containing a polyethylenimine compound (Samples 3B) showed a significantly lower acetaldehyde concentration than the virgin, untreated polyol (Sample 3A).

Example 4

This example demonstrates the production of a composition according to the invention.

A TDI-MDI molded polyurethane foam was produced by mixing the components listed in Table 4 below. To produce the foam, the sodium bisulfite/PEI (if present) were added to the water and the resulting mixture was added to a beaker containing the polyol. The resulting mixture was stirred at ambient temperature for approximately 30 seconds at 4,000 rpm. Next, the other components in Table 4 (except the isocyanate (TM80)) were added to the beaker and stirred at ambient temperature for approximately 30 seconds at 4,000 rpm. The isocyanate was then added to the beaker, and the mixture was stirred for an additional 5-10 seconds at 4,000 rpm. The mixture was then cast into a mold that was maintained at approximately 75° C. in a water bath. After an approximately 5 minute cure, the mold was removed from the water bath, and the foam was removed from the mold.

TABLE 4

Foam formulation for Samples 4A-4I.

| Component | Amount |
|---|---|
| Polyol | 158 g |
| Grafted Polyol | 68 g |
| Triethylenediamine (33%) | 0.6 mL |
| Diethanolamine | 3.4 g |
| Niax Catalyst EF-150 (Momentive) | 0.72 g |
| Niax Y-10366 foam stabilizer (Momentive) | 2.2 g |
| Water | 8 mL |
| Sodium bisulfite (NaHSO$_3$) | As noted in Table 5 |
| Polyethylenimine (PEI) | As noted in Table 5 |
| TM80 (TDI:PM200 = 80:20) | 106 g |

TABLE 5

Additive content (expressed as ppm based on the polyol content) and corresponding reduction in aldehyde content for Samples 4A-4I.

| | Additive Content (ppm) | | Reduction in Aldehyde content (%) | |
|---|---|---|---|---|
| Sample | PEI | NaHSO$_3$ | Formaldehyde | Acetaldehyde |
| 4A | 1,000 | 0 | 4.2 | 1.0 |
| 4B | 2,000 | 0 | 0 | 0 |
| 4C | 0 | 1,000 | 92.9 | 45.3 |
| 4D | 0 | 2,000 | 89.6 | 37.1 |
| 4E | 500 | 500 | 90.0 | 70.0 |
| 4F | 500 | 1,000 | 92.4 | 73.5 |
| 4G | 1,000 | 500 | 89.0 | 69.0 |
| 4H | 1,000 | 1,000 | 90.4 | 68.5 |
| 4I | 2,000 | 1,000 | 89.7 | 71.0 |

As can be seen from the data in Table 5, the polyurethane foams containing sodium bisulfite exhibited appreciable reductions in both formaldehyde and acetaldehyde content. However, a comparison of the data for Samples 4C-4I shows that the observed reduction of acetaldehyde increased dramatically when polyethylenimine was added to the formulation. This result is surprising given the fact that adding PEI alone produced no or only a negligible decrease in acetaldehyde content in the foam. Indeed, the results suggest an unexpected synergistic effect from the combination of polyethylenimine and sodium bisulfite.

Example 5

This example demonstrates the production of a composition according to the invention.

An MDI molded polyurethane foam was produced by mixing the components listed in Table 6 below. To produce the foam, the sodium bisulfite/PEI (if present) were added to the water and the resulting mixture was added to a beaker containing the polyol. The resulting mixture was stirred at ambient temperature for approximately 30 seconds at 4,000 rpm. Next, the other components in Table 6 (except the isocyanate (PMDI)) were added to the beaker and stirred at ambient temperature for approximately 30 seconds at 4,000 rpm. The isocyanate was then added to the beaker, and the mixture was stirred for an additional 5-10 seconds at 4,000 rpm. The mixture was then cast into a mold that was maintained at approximately 75° C. in a water bath. After an approximately 5 minute cure, the mold was removed from the water bath, and the foam was removed from the mold.

TABLE 6

Foam formulation for Samples 6A-6I.

| Component | Amount |
|---|---|
| Polyol | 200 g |
| Triethylenediamine (33%) | 0.74 mL |
| Diethanolamine | 3 g |
| Niax catalyst C-225 (Momentive) | 0.5 g |
| Niax Silicone L-3627 surfactant (Momentive) | 2 g |
| Water | 8 mL |
| Sodium bisulfite (NaHSO$_3$) | As noted in Table 5 |
| Polyethylenimine (PEI) | As noted in Table 5 |
| Polymeric MDI | 178 g |

TABLE 7

Additive content (expressed as ppm based on the polyol content) and corresponding reduction in aldehyde content for Samples 6A-6I.

| Sample | Additive Content (ppm) | | Reduction in Aldehyde content (%) | |
|---|---|---|---|---|
| | PEI | NaHSO₃ | Formaldehyde | Acetaldehyde |
| 6A | 1,000 | 0 | 24.6 | 1.7 |
| 6B | 2,000 | 0 | 36.2 | 6.4 |
| 6C | 0 | 1,000 | 91.0 | 26.7 |
| 6D | 0 | 2,000 | 97.0 | 87.7 |
| 6E | 500 | 500 | 92.3 | 65.4 |
| 6F | 500 | 1,000 | 96.5 | 86.3 |
| 6G | 1,000 | 500 | 93.6 | 74.8 |
| 6H | 1,000 | 1,000 | 96.3 | 94.6 |
| 6I | 2,000 | 1,000 | 95.5 | 92.2 |

As can be seen from the data in Table 7, the polyurethane foams containing sodium bisulfite exhibited appreciable reductions in both formaldehyde and acetaldehyde content. However, a comparison of the data for Samples 6C-6I shows that the observed reduction of acetaldehyde increased even further when polyethylenimine was added to the formulation. This result is surprising given the fact that adding PEI alone produced no or only a negligible decrease in acetaldehyde content in the foam. Indeed, the results suggest an unexpected synergistic effect from the combination of polyethylenimine and sodium bisulfite.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A method for producing a polyurethane polymer comprising the steps of:
    (a) providing a polyol composition, the polyol composition comprising:
        (i) a polyol,
        (ii) a polyethylenimine compound; and
        (iii) a bisulfite compound;
    (b) providing an isocyanate compound;
    (c) providing a catalyst;
    (d) combining and reacting the polyol composition, the isocyanate compound, and the catalyst to produce a polyurethane polymer.

2. The method of claim 1, wherein the polyol has a molar mass of about 400 g/mol or more.

3. The method of claim 1, wherein the polyol is a polyether polyol.

4. The method of claim 1, wherein the polyethylenimine compound has a molar mass of about 500 g/mol or more.

5. The method of claim 1, wherein the polyethylenimine compound preferably is present in the polyol composition in an amount of about 50 ppm or more, based on the weight of the polyol present in the polyol composition.

6. The method of claim 5, wherein the polyethylenimine compound is present in the polyol composition in an amount of about 50 ppm to about 3,000 ppm, based on the weight of the polyol present in the polyol composition.

7. The method of claim 1, wherein the bisulfite compound is present in the polyol composition in an amount of about 50 ppm or more, based on the weight of the polyol present in the polyol composition.

8. The method of claim 7, wherein the bisulfite compound is present in the polyol composition in an amount of about 50 ppm to about 3,000 ppm, based on the weight of the polyol present in the polyol composition.

9. The method of claim 1, wherein the bisulfite compound is sodium bisulfite.

* * * * *

UNITED STATES PATENT AND TRADEMARK OFFICE
CERTIFICATE OF CORRECTION

PATENT NO. : 11,578,027 B2
APPLICATION NO. : 17/028216
DATED : February 14, 2023
INVENTOR(S) : Chunping Xie et al.

It is certified that error appears in the above-identified patent and that said Letters Patent is hereby corrected as shown below:

In the Claims

In Column 10, Line 38, Claim 5 after the word "compound" delete the word "preferably"

Signed and Sealed this
Twenty-fourth Day of October, 2023

Katherine Kelly Vidal
*Director of the United States Patent and Trademark Office*